United States Patent [19]

Hay-Kaufman et al.

[11] Patent Number: 4,818,677

[45] Date of Patent: Apr. 4, 1989

[54] MEMBRANE ASSAY USING FOCUSED SAMPLE APPLICATION

[75] Inventors: Martha L. Hay-Kaufman, Los Altos; Rosette Becker, Palo Alto; Robert Danisch, Fremont, all of Calif.

[73] Assignee: Monoclonal Antibodies, Inc., Mountain View, Calif.

[21] Appl. No.: 128,257

[22] Filed: Dec. 3, 1987

[51] Int. Cl.$^4$ .................... G01N 33/53; G01N 33/569
[52] U.S. Cl. ............................... 435/4; 422/56; 422/58; 435/5; 435/6; 435/7; 435/805; 435/810; 436/810; 436/813
[58] Field of Search .................. 435/7, 805, 810, 4, 435/5, 6; 436/810, 813; 422/56, 58

[56] References Cited

U.S. PATENT DOCUMENTS

| | | | |
|---|---|---|---|
| 3,888,629 | 6/1975 | Bagshawe | 23/230 B |
| 4,366,241 | 12/1982 | Tom et al. | 435/7 |
| 4,631,174 | 12/1986 | Kondo | 436/810 X |
| 4,632,901 | 12/1986 | Valkirs et al. | 435/5 |

FOREIGN PATENT DOCUMENTS 0264036  4/1988  European Pat. Off. .

OTHER PUBLICATIONS

Package Insert–TestPack®, Abbott Laboratories, North Chicago, Ill. 60064, 2 pages.

*Primary Examiner*—Sidney Marantz
*Attorney, Agent, or Firm*—Townsend & Townsend

[57] ABSTRACT

Methods and kits are described for performing immunoassays. The kit includes a reaction cell having a microporous membrane and an absorbent capable of drawing liquid sample through the membrane. An applicator is provided for applying a small volume of the liquid sample to the membrane by contacting a port of the applicator to the membrane and allowing the sample to flow therethrough by capillary action. Analyte in the sample is immobilized, typically by immunoadsorption, and the immobilized analyte may then be visualized using conventional signal producing systems, such as color, fluorescence, and luminescent systems.

47 Claims, 3 Drawing Sheets

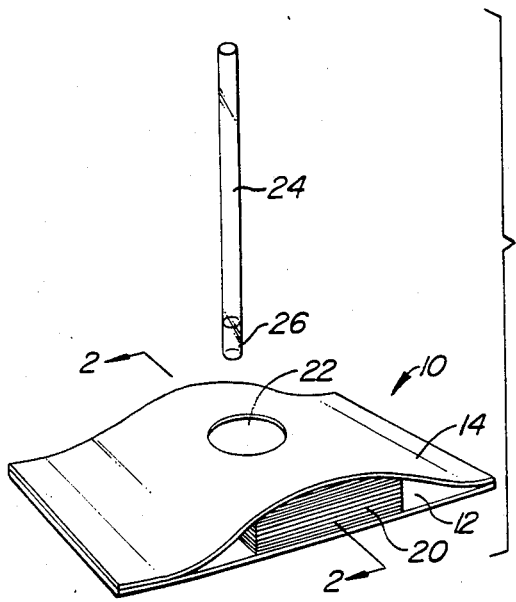
FIG._1.
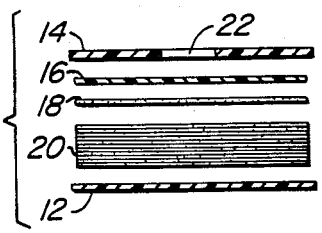
FIG._2.
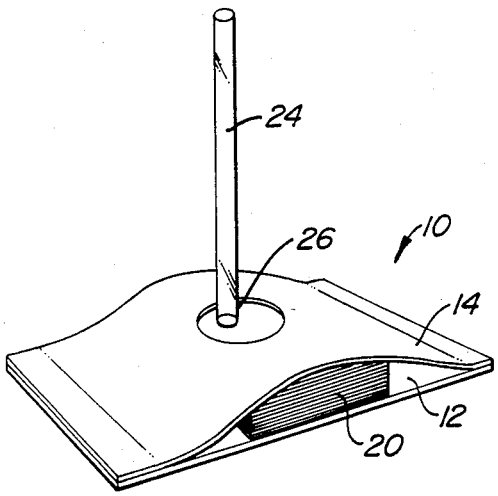
FIG._3.
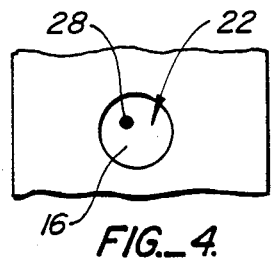
FIG._4.
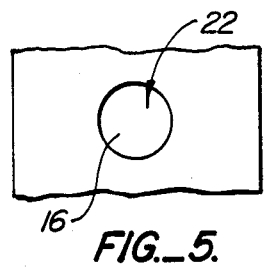
FIG._5.

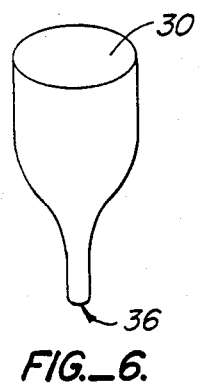
FIG._6.
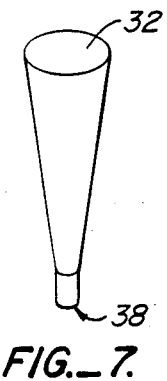
FIG._7.
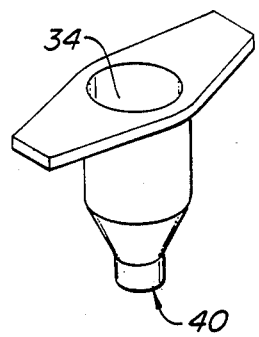
FIG._8.
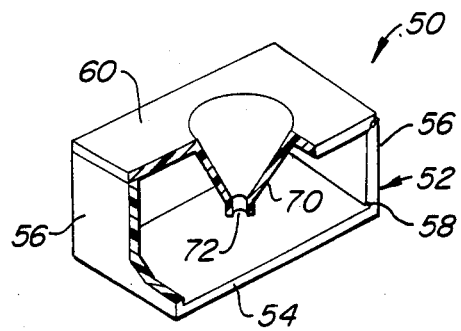
FIG._9.
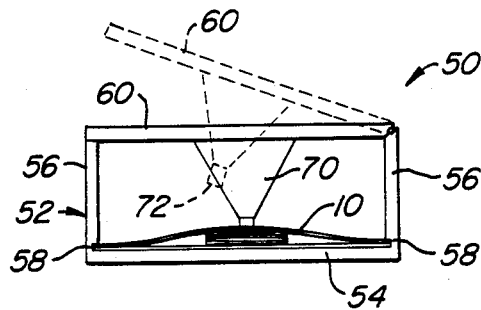
FIG._10.

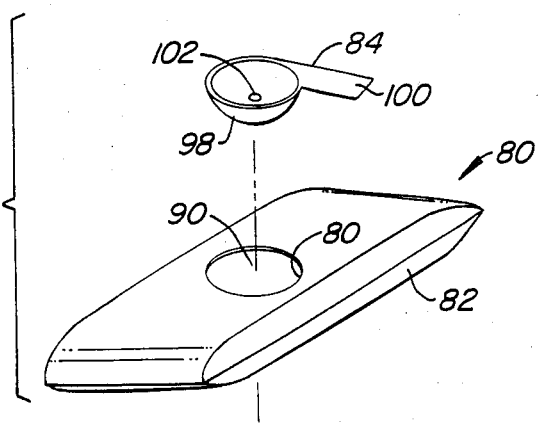
FIG._11.
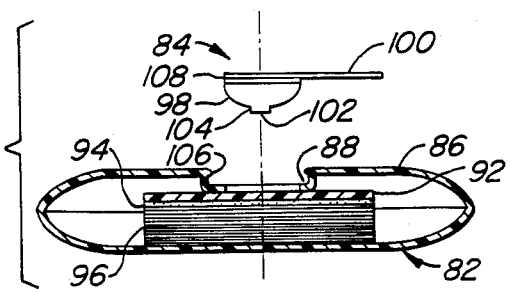
FIG._12.
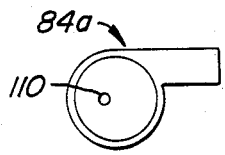
FIG._13.
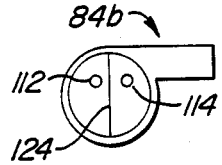
FIG._14.
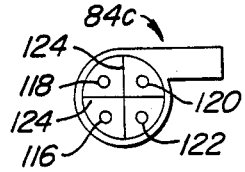
FIG._15.

MEMBRANE ASSAY USING FOCUSED SAMPLE APPLICATION

BACKGROUND OF THE INVENTION

1. Field of the Invention

The present invention relates generally to assay methods, and more particularly to solid phase membrane assays employing visual labels.

2. Description of the Background Art

A wide variety of immunoassay methods have been developed for detecting and quantitating numerous analytes in liquid samples. Such assays may generally be classified in the following categories: competitive or non-competitive, homogeneous (liquid phase) or non-homogeneous (solid phase), and according to label such as radioactive or visual label. The present invention is particularly concerned with methods and kits for performing non-homogeneous (solid phase) assays employing visual labels, particularly color labels, by both competitive and non-competitive techniques.

A large number of assays have been developed even within the limited category just described. For example, U.S. Pat. Nos. 3,888,629; 4,366,241; and 4,632,901, each describe assays employing a membrane immunoadsorbent in combination with an absorbent pad. Liquid sample is applied to the pad by various techniques, and the sample drawn through the entire membrane area by capillary action of the absorbent pad. The membrane is exposed to labelled antibody, and binding of the labelled antibody to the membrane is proportional to the amount of analyte in the sample. Assays of this type are particularly convenient for performance outside of clinical laboratories as they require few steps, short incubation times, and the materials are readily disposable (at least if non-radioactive labels are employed). Heretofore, however, such assays have been generally unsuitable for samples characterized by very low analyte concentrations and/or very low sample volumes where the analyte is bound to the membrane at very low levels. Frequently, the signal observed on the membrane pad is so weak that it is impossible to tell whether analyte was present in the sample.

It would therefore be desirable to provide methods and kits for performing membrane assays having improved sensitivity and readability. It would be particularly desirable if such methods and kits retained the convenience, economy and rapid performance characteristic of previous membrane assays.

SUMMARY OF THE INVENTION

The present invention provides a method and kit for performing non-radioisotopic membrane assays having improved sensitivity and readability. By focusing passage of a sample through a limited area on a membrane, analyte may be concentrated within said area to provide a strong visual signal which contrasts sharply with the surrounding area of the membrane after the membrane has been developed. Alternatively, such improved sensitivity may be achieved by focusing one or more components of a reagent system used to produce the visual signal within a similar limited area on the membrane, even when the sample has been applied in a non-focused manner. Using the present invention, analyte concentrations are low as 1 ng/ml, and below, may be detected in sample volumes as low as 1 $\mu$l. Such sensitivity is particularly useful in viral and bacterial assays where the analytes is often present in very low concentrations, and in pediatric and other cases where sample volume may be quite limited.

The present invention employs a reaction cell including a microporous membrane and, usually, an absorbent located adjacent the membrane and able to draw liquid therethrough. The membrane is capable of separating and immobilizing analyte as sample passes therethrough, and may include covalently or non-covalently bound specific binding substances, usually antibodies specific for the analyte. A predetermined volume of a liquid sample suspected of containing analyte is passed through the membrane within a limited, well-defined area so that outward diffusion of the analyte in the sample from the area is inhibited. In this way, the analyte is concentrated within the limited area, providing for an enhanced visual signal having improved contrast and delineation relative to the surrounding membrane, upon subsequent development. Alternatively, the sample may be passed through the membrane in a non-focused manner and one or more components of the visual signal reagent system applied within a similar limited, well-defined area. It is also possible to apply both the sample and reagent component(s) in a focused manner, but only marginal improvement is normally gained.

In the preferred embodiment, the liquid sample and/or visual reagent component(s) is applied with an applicator having a port with an area in the range from about 0.5 to 20 mm$^2$, usually in the range from about 1 to 10 mm$^2$. Typically, the port will have a substantially circular periphery with a diameter in the range from about 0.5 to 5 mm, usually in the range from about 1 to 3 mm. The sample is drawn from the applicator by capillary action of the absorbent, and it has been found that outward diffusion of the analyte in the sample within the membrane is negligible. Thus, the analyte is bound only within the area defined by the port of the applicator.

In a particularly preferred embodiment, the applicator is a simple capillary tube having a diameter equal to that of the desired port diameter. The capillary tube is used first to draw a predetermined volume of the liquid sample and/or visual reagent component(s) and then to apply the volume to the microporous membrane. Alternatively, the applicator can be a focusing tube, such as a conical tube or funnel. The sample and/or visual reagent component(s) is drawn using a fluid dropper or similar device and applied to the membrane using the focusing tube which concentrates the sample and/or visual reagent component(s) through its port. The focusing tube may include two or more ports, allowing different samples and/or visual reagent component(s) to be applied to different areas on the membrane in a single test procedure.

Desirably, a porous, non-absorbent layer is disposed between the membrane and the absorbent. Such a non-absorbent layer provides for improved contrast as it prevents read-through which might otherwise result from visual signal being generated in the absorbent. Visualization of the membrane is accomplished with conventional reagent systems, typically providing for a color, fluorescent, or luminescent signal.

BRIEF DESCRIPTION OF THE DRAWINGS

FIG. 1 illustrates the construction of a reaction cell and an applicator according to the principles of the present invention.

FIG. 2 is an exploded, cross-section view of the reaction cell taken along line 2—2 of FIG. 1.

FIG. 3 illustrates the manner of applying a sample to the membrane of the reaction cell using a capillary tube applicator according to the present invention.

FIG. 4 illustrates the membrane of the reaction cell after a positive test, depicting a well-defined visual signal.

FIG. 5 illustrates the membrane of the reaction cell of the present invention after a negative test where no visual signal has been produced.

FIGS. 6 through 8 illustrate alternative embodiments of the applicator of the present invention.

FIGS. 9 and 10 illustrate an applicator system which can be used to both hold a reaction cell and apply liquid sample to the cell while it is being held.

FIGS. 11 and 12 illustrate the construction of a reaction cell having a detachable focusing member.

FIGS. 13, 14, and 15 illustrate alternative designs for the detachable focusing member of FIGS. 11 and 12.

DESCRIPTION OF THE SPECIFIC EMBODIMENTS

A method and kit are provided for performing immunoassays. The method utilizes a reaction cell including a microporous membrane which is capable of separating and immobilizing an analyte as a fluid sample is passed therethrough. By applying the fluid sample to a relatively small, well-defined area on the membrane in a manner which limits outward diffusion of analyte in the sample, the analyte is focused or concentrated within said area. The presence of the immobilized analyte within the membrane may then be detected by conventional visualization systems, particularly those systems which result in a color fluorescent, or luminescent signal. The focusing of the analyte within the limited area on the membrane provides improved sensitivity and readability of the assay. Additionally, it has been found that improved sensitivity and readability may be achieved by applying one or more components of the visualization system to a similar small, well-defined area on the membrane.

The method and kit of the present invention are particularly useful for the performance of assays by untrained and semi-trained individuals. Sample preparation is usually minimal, and the assay method steps may be easily performed by an individual reading a set of instructions accompanying the assay kit. The enhanced sensitivity and readability of the assay are particularly helpful in assuring that the test results are easily read and understood even by untrained persons.

The present invention is useful in assaying for a wide variety of analytes in virtually any type of sample which is liquid, which can be liquified, or which can be suspended in a liquid. The method and kit will find their greatest use with biological specimens, such as blood, serum, plasma, urine, cerebral fluid, spinal fluid, ocular lens liquid (tears), saliva, sputum, semen, cervical mucus, scrapings, swab examples and the like. Use will also be found with industrial, environmental, and food samples, such as water, process streams, milk, meat, poultry, fish, and the like. Under certain circumstances, it may be desirable to pretreat the sample, such as by liquification, separation, dilution, concentration, filtration, chemical treatment, or a combination thereof, in order to improve the compatibility of the sample with the assay. The selection and pretreatment of biological, industrial, and environmental samples prior to immunological testing is well known in the art and need not be described further.

The analyte to be detected may be virtually any compound, composition, aggregation, or other substance which may be immunologically detected. That is, the analyte, or a portion thereof, will be antigenic or haptenic having at least one determinant site, or will be a member of a naturally-occurring binding pair, e.g., carbohydrate and lectin, hormone and receptor, complementary nucleic acids, and the like. Analytes of particular interest include antigens, antibodies, proteins, carbohydrates, haptens, drugs, hormones, macromolecules, toxins, bacteria, viruses, enzymes, tumor markers, nucleic acids, and the like, although other types of substances may also be detected. A non-exhaustive list of exemplary analytes is set forth in U.S. Pat. No. 4,366,241, at column 19, line 7 through column 26, line 42, the disclosure of which is incorporated herein by reference. The detection of human chorionic gonadotropin (hCG) and herpes simplex virus are exemplified in the Experimental section, hereinafter.

The reaction cell of the present invention includes a microporous membrane and an absorbent in liquid receiving relationship with the membrane. The microporous membrane is intended to separate and immobilize the analyte from the sample as it passes from the applicator through to the absorbant. The shape and dimensions of the membrane are not critical, but the membrane should have a sufficiently large exposed area to allow visualization of a sample on a portion thereof with sufficient excess area so that contrast between the visual signal and the remainder of the membrane may be easily observed. Typically, the membrane will have an exposed area in the range from about 0.2 to 2.0 $cm^2$, more usually in the range from about 0.25 to 1.5 $cm^2$. The membrane may also include an area which is not exposed. That is, a portion of the membrane may be covered by a structural element or other component of the reaction cell so that it is not observable.

The microporous membrane may be formed from a wide variety of semipermeable membrane materials, including organic polymers, such as nylon, polyvinylchloride, polypropylene, and copolymers thereof; sintered glass and ceramic materials; and the like. The average pore diameter of the material is usually not critical, although materials having particular pore diameters may be selected to immobilize bacteria and viruses without the use of bound specific binding substances. Pore diameters in the range from about 0.2 to 10 $\mu m$ will generally be suitable, usually being in the range from about 1 to 5 $\mu m$.

For most applications, specific binding substances will be bound to the microporous membrane to facilitate separation of the analyte of interest. Such specific binding substances will usually be antibodies capable of binding antigens and haptens, although antigens, hormone receptors, lectins, polysaccharides, nucleic acids, and other natural receptors and ligands may also find use. Methods for binding the specific binding substances to the microporous membrane are well known and amply described in the scientific and patent literature.

Generally, the specific binding substances will be bound at a uniform concentration across the entire membrane surface, although under certain circumstances it may be desirable to bind the substances on only a portion of the membrane surface. Moreover, it may be desirable to sometimes bind more than one specific binding substance to the membrane, with substances having different specificities being bound in the same or different areas of the membrane.

A particular protocol for uniformly binding anti-α-hCG antibody to a nylon membrane having an average pore diameter of 3 μm is described in the Experimental section hereinafter.

The absorbent will be located adjacent one face of the microporous membrane in order to draw liquids therethrough by capillary action. The primary requirement of the absorbent is that it be capable of absorbing liquid sample in an amount substantially greater than that which would be expected to be applied during any one test. Suitable absorbent materials include cellulose products, particularly cellulose acetate, paper, cotton, and the like; various dried gels, such as silica gel, agarose, dextran, gelatin; porous polyethylene; and the like. In the exemplary embodiment, the absorbent comprises layers of non-woven cellulose.

As an alternative to the absorbent, it is also possible to employ a vacuum source, such as a Buchnel funnel, for drawing the liquid sample through the membrane. Although generally more cumbersome than the use of an absorbent, use of a vacuum source might be preferable in automated systems where large numbers of samples are being simultaneously processed.

The reaction cell may optionally include a spacer layer between the microporous membrane and the absorbent. The spacer layer will also be porous, but will be generally incapable of binding the analyte of interest. The purpose of the spacer layer is to provide separation between the membrane and the absorbent so that signal which develops in the absorbent is not visible through the membrane. Suitable spacer layers may be formed from a non-woven polyester, a porous polyethylene, or other porous material which will not absorb the signal generated in the absorbent during the assay.

The applicator of the present invention will be capable of holding a preselected sample and/or visual reagent component(s) volume and passing the volume to the membrane through a port having a preselected geometry and size. Usually, the sample volume will be in the range from about 1 to 1000 μl, more usually in the range from 10 to 500 μl, and typically in the range from about 25 to 250 μl. Volume(s) for the visual reagent component(s) may vary widely, but will usually be in the range from 25 to 1000 μl. The port area is usually in the range from about 0.5 mm² to about 20 mm², more usually being in the range from about 1 mm² to 10 mm². Conveniently, the applicator is a capillary tube defining a circular port having a diameter in the range from about 0.5 to 5 mm in diameter, usually in the range from about 1 to 3 mm in diameter. The capillary tube applicator may be graduated to allow precise control of the sample and/or visual reagent component(s) volume. Alternatively, volume may be controlled by carefully sizing the internal capillary diameter so that a desired volume is held in the tube by capillary action.

Generally, when applying the liquid sample to the reaction cell membrane with a capillary tube applicator, the absorbency of the absorbent will be relied on to draw the liquid from the tube without additional means. Optionally, a pressure bulb may be provided on the end of the capillary tube so that the liquid may be expelled from the capillary through the membrane under a positive pressure.

Alternatively, the applicator may be a focusing tube having a relatively large opening at its top and one or more smaller openings defining port(s) at its bottom. The focusing tube can be used to focus liquid samples and/or visual reagent component(s) by placing the port on the membrane of the reaction cell and thereafter applying liquid through the upper opening. Conveniently, the liquid can be applied through the focusing tube with a fluid dropper. In a particular embodiment, as described in more detail hereinafter, the focusing tube is incorporated in an applicator system which holds a reaction cell in a predetermined position relative to the port. The liquid sample and/or visual reagent component(s) can thus be precisely and repeatedly positioned on the membrane so that a reference standard can be located at a second position on the membrane without interference.

Focusing tubes having multiple ports may find use under a variety of circumstances. For example, different samples may be applied to different areas on a single membrane. Different samples would include not only samples from different patients, but also different dilutions of the same sample from a single patient, reference samples, and the like. Also, it would be possible to apply a single sample to the entire membrane, and then apply different visual reagent components to different areas on the membrane. In that way, a number of analytes could be tested for at the same time. Many other instances will also rise where it is desirable to apply different substances to different areas on the membrane where a focusing tube having multiple ports will also find use.

Signal producing systems capable of generating a detectable visual change on the membrane surface (referred to herein as "visual labels") include color-generating systems, fluorescent systems, and luminescent systems. Suitable signal producing systems will include at least one component and may comprise two or more components including enzymes, substrates, catalysts, enhancers, and the like. Usually, at least one component of the signal producing system will be attached to a specific binding substance which can be introduced to the membrane and bind to immobilized analyte, if any, in non-competitive assay protocols. Examples of non-competitive assays include sandwich assays, fluorescent antibody assays, enzyme-linked immunosorbent assays (ELISA's), and the like. Alternatively, the label may be bound to analyte or an analyte analog and used in a competitive signal detection protocol. That is, the labelled analyte will be introduced to the membrane and will produce a signal inversely proportional to the amount of analyte present in the sample.

Numerous suitable signal producing systems are described in U.S. Pat. No. 4,366,241 at column 27, line 35 through column 36, line 63, the disclosure of which is incorporated herein by reference.

Preferred are the use of color-producing systems which result in the deposition of a dye within the limited area on the membrane defined by the port geometry of the applicator. In examples which follow, antibody conjugated to alkaline phosphatase is exposed to the membrane after the analyte has been immobilized. Subsequent exposure of the membrane to an indoxyl phosphate substrate results in deposition of a dark blue dye on the membrane surface. High contrast between the dyed and undyed portions of the membrane surface allows for very sensitive analyte detection.

Referring now to FIGS. 1 and 2, a reaction cell 10 includes a base panel 12 and upper panel 14. Interposed between the panels 12 and 14 are a microporous membrane member 16, a spacer layer 18, and an absorbent 20 comprising a plurality of layers of non-woven cellulose. Conveniently, the base and upper panels 12 and 14 are formed from a thermoplastic, such as polystyrene, and may be heat sealed along thier edges to form the reaction cell 10. Upper panel 14 includes an aperture 22 which exposes the upper surface of membrane 16 of the outside of reaction cell 10. Applicator 24 comprises a glass, plastic or other rigid capillary tube having a port diameter in the range from about 0.5 to 5 mm and a length in the range from about 3 to 15 cm.

Referring now to FIG. 3, a predetermined volume of the sample to be tested is drawn into the capillary by simply immersing the capillary tip into a reservoir of the sample (not illustrated). The sample is then transferred to the reaction cell, where the tip 26 of the capillary tube 24 is pressed gently against the upper surface of membrane 16 through aperture 22. The sample begins flowing downward into the absorbent 20 immediately as a result of capillary action. As the sample flow through the membrane 16, any analyte in the sample is specifically or non-specifically bound to the membrane, as described above. The sample and any remaining analyte then flow through the spacer layer 18 and into the absorbent 20, with minimal binding of the analyte to the spacer layer 18.

At least some of the component of the labelling reagent system may be added directly after sample addition. For example, labelled antibody specific for the analyte may be added, and allowed to incubate for a short period, typically about one to six minutes. The capillary tube 24 may also be used for the addition of such component(s), but it will be necessary to carefully align the area of application so that analyte is present for detection. Alternatively, the sample can be applied in a non-focused manner, e.g., with a fluid dropper, and only the labelling reagent system component(s) applied with the capillary.

After addition of labelled antibody, the membrane is optionally washed, typically with several drops of a wash solution, such as water or a buffer, and substrate for the enzyme label added and allowed to incubate, again for about one to six minutes. Optionally, the reaction may be stopped by addition of an appropriate stop solution, in order to preserve the test result on the reaction cell. The signal may then be read without further process steps. If the sample is positive, a visible spot 28 will appear on the membrane 16, as illustrated in FIG. 4. The spot will be intense relative to similar signals in prior art methods where the sample would have been added with a fluid dropper or other unfocused applicator directly onto the substrate. In addition, a sharp contrast will be present between the spot and the surrounding membrane. If the sample had been free from analyte, the results would appear as in FIG. 5. That is, no spot would be developed.

Alternate liquid sample applicators are illustrated in FIGS. 6–8. In each case, the applicator is generally a conical tube having a relatively large inlet opening (30, 32, and 34 in FIGS. 6, 7, and 8, respectively) and a smaller outlet port 936, 38, and 40 in FIGS. 6, 7, and 8, respectively). Such conical tube applicators act to focus the liquid sample onto an area on the reaction cell membrane defined by the geometry of the smaller outlet port and hence are referred to as focusing tubes herein. The outlet port 36, 38, or 40 is contacted against the membrane 22 of the reaction cell 10, and liquid sample thereafter introduced through the inlet opening 30, 32, or 34. The liquid sample will usually be introduced by a fluid dropper, measuring spoon, or similar fluid transfer device (not illustrated). Alternatively, the sample may be poured in the inlet of the focusing tube opening from another receptacle, such as a test tube or vial. Liquid sample entering the focusing tubes will be drawn through the membranes 22 of the reaction cell 10 as described for the capillary tube applicator above. Generally, the focusing tubes are useful with relatively large sample volumes and the capillary tubes are useful with large and small sample volumes.

A particular applicator system 50 is illustrated in FIGS. 9 and 10. The applicator system 50 includes a U-shaped frame 52 including a bottom panel 54 and side panels 56. A slot 58 is formed in each of the side panels 56 adjacent the intersection of the side panel with the bottom panel 54. As observed in FIG. 10, the frame 52 is dimensioned to receive the reaction cell 10 in the slots 58. A top panel 60 is hinged onto one of the side panels 56 so that it may be raised from a closed position (shown in full line in FIG. 10) to an open position (shown in broken line in FIG. 10).

A conical focusing tube 70 is secured to the top panel 60 and positioned so that a port 72 formed at the lower end of the focusing member will contact a preselected area on the membrane 22 of the reaction cell 10 when the top panel 60 is lowered into its closed position. Liquid sample may then be applied to the preselected area on the membrane by transferring said sample through the focusing tube 70 as described above for the conical focusing tubes of FIGS. 6, 7, and 8. Use of the applicator system 50 is advantageous in that it allows sample and/or component(s) of the labelling regent system to be precisely and repeatedly applied to a particular predefined area on the membrane, leaving the remaining areas free for other uses, such as application of a standard solution or other samples.

Although not illustrated, the focusing tube 70 of applicator system 50 could include more than one port 72. Usually, although not necessarily, if more than one port is present, barriers will be provided so that different liquids can be passed through each of the ports without cross-contamination.

A reaction cell system 80 including a reaction cell 82 and a detachable focusing member 84 is illustrated in FIGS. 11 and 12. The reaction cell 82 includes an enclosed case 86 having a well 88 formed in its upper surface. An aperture 90 is formed in the bottom of the well 88 and exposes a portion of membrane 92 which is held within the case 86. A spacer layer 94 is placed beneath the membrane 92, and absorbent layers 96 are disposed beneath the spacer layer. The characteristics of the membrane 92, spacer layer 94, and absorbent layers 96 are essentially the same as those of the analogous components of rection cell 10 described previously.

The focusing member 84 includes a bowl or receptacle 98 and a handle 100. A port 102 is formed at the bottom of the bowl 98.

The focusing member 84 is received into the well 88 on the reaction cell 82 so that the port 102 firmly contacts the membrane 92. Usually, a lip 104 is formed about the port 102 so that the port seals against the membrane 92. In that way, leakage around the port is avoided.

Conveniently, provision is made to hold the focusing member 84 in place within the well 88. For example, a detent 106 may be formed about the periphery of the well 88, and an annular groove formed about the upper portion of the bowl 98 of focusing member 84. The focusing member 84 may then simply be snapped in place within the well 88.

Focusing members 84 having alternate constructions are illustrated in FIGS. 13, 14, and 15. Focusing member 84a includes a port 110 which is offset from center. That leaves a portion of the membrane free for other uses, as discussed above. Focusing members 84b and 84c have multiple ports 112, 114, 118, 120, and 122. In each case, barriers 124 are provided so that liquids may be selectively applied through individual ports without cross-contamination.

The method of the present invention is particularly suitable for home and small medical office use, and it is contemplated that the reaction cell and sample applicator just described may be sold together in a kit. In addition to the reaction cell and applicator, the kit will include the necessary components of the signal producing system, typically separated into small vials. The kit will also include instructions on how to perform the assay in a manner consistent with the method as just described. In particular, the instructions will describe to the user that the sample is to be applied to the membrane using an applicator having a relatively small port by capillary action, as just described.

The following examples are offered by way of illustration, not by way of limitation.

EXPERIMENTAL

Comparisons of the focused sample membrane assays of the present invention with otherwise comparable unfocused sample assay protocols were performed for the detection of both human chorionic gonadotropin (hCG) and the herpes simplex virus) (HSV). Using capillary tube addition, improved dose response and sensitivity were obtained together with a reduction of the reaction time required to perform the assay.

Materials and Methods

All assays were performed using a reaction cell as illustrated in FIGS. 1–3. Aperture 22 was approximately 10 m in diameter for the HSV assay and 13 mm in diameter for the hCG assay. Membrane 16 was nylon having an average pore diameter of approximately 3 $\mu$m. A non-woven polyester spacer layer 18 having a thickness of approximately 0.1 mm was employed, together with a layered non-woven cellulose absorbent.

For the HSV assay, the nylon membrane 16 was not modified. For the hCG assay, mouse monoclonal $\alpha$-hCG antibody specific for the beta subunit was on the nylon membrane 16.

The applicator used in performing the focused sample assays of the present invention was a polypropylene capillary tube having an internal diameter of approximately 2.5 mm and a length of approximately 95 mm. A standard fluid dropper was used to apply liquid sample to the membrane of the reaction cell in the unfocused sample assays.

The hCG assay was a two-site, enzyme-linked immunospecific assay. Sediment-free urine samples were applied to the membrane of the reaction cell, either using the capillary tube applicator for the focused sample assays or using a fluid dropper for the unfocused sample assays. When using the capillary tube, care was taken to evenly contact the open lower port of the capillary tube so that sample liquid would not spread over the upper surface of the membrane.

Immediately, after applying the urine sample, a reagent solution (300 $\mu$l) including hCG-specific mouse monoclonal IgG covalently linked to alkaline phosphatase with stabilizers and sodium azide. After a preselected time, the membrane was washed with a buffer (450 $\mu$l), and thereafter a substrate solution of indoxyl phosphate (150 $\mu$l) was added. After two minutes, the matrix was observed for a color change.

The HSV was similar, except that the membrane of the reaction cell was free from specific-binding substances, and HSV binding was detected using HSV-specific mouse monoclonal antibody covalently linked to alkaline phosphatase with stabilizers and sodium azide.

Results 1. hCG Assays

A first series of tests were performed using urine samples having known hCG concentrations. Samples of six known concentrations were applied to reaction cells using either the capillary tube (25 $\mu$l volume) or a fluid dropper 925 $\mu$l and 300 $\mu$l volumes). Optical density measurements were taken with a Macbeath TD904 Transmission Densitometer. The results are set forth in Table 1.

TABLE 1

| Conc. of hCG (mIU/ml) | $\Delta$O.D.* | | |
|---|---|---|---|
| | 25 $\mu$l (Cap.) | 25 $\mu$l (Drop.) | 300 $\mu$l (Drop.) |
| 0 | 0.04 | 0.01 | 0.01 |
| 12.5 | 0.05 | 0.01 | 0.02 |
| 25 | 0.11 | 0.02 | 0.03 |
| 50 | 0.16 | 0.00 | 0.13 |
| 100 | 0.50 | 0.02 | 0.24 |
| 200 | 0.56 | 0.06 | 0.25 |

*Difference in optical density between background and reaction area with reaction stopped at two minutes after substrate addition by washing the membrane with stop solution (50 mM EDTA).

From Table 1, it can be observed that focusing the liquid sample provides a substantial increase in the intensity of the signal observed for each of the sample concentrations tested. The $\Delta$O.D. observed for a 25 $\mu$l sample applied by the capillary tube applicator was consistently greater than for dropwise addition, even with a sample size 12 times greater. For an equivalent sample size (25 $\mu$l), the observed $\Delta$O.D. for the capillary tube applicator at 12.5 mIU/ml was approximately equal to that observed with dropwise addition at 200 mIU/ml.

A second series of tests was performed to compare the reaction kinetics of focused sample addition with those of dropwise sample addition. Sample (25 $\mu$l) having an hCG concentration of 200 mIU/ml was applied to the reaction cell using both the capillary tube applicator and a fluid dropper. The $\Delta$O.D's developed at various incubation periods between 0 and ten minutes were observed and recorded. The results are set forth in Table 2.

TABLE 2

| Elapsed Time* | $\Delta$O.D. | |
|---|---|---|
| | Capillary | Fluid Dropper |
| 0 | 0.00 | 0.00 |
| 0.5 sec. | 0.07 | 0.00 |
| 1 | 0.20 | 0.01 |
| 2 | 0.40 | 0.01 |
| 5 | 1.19 | 0.20 |
| 10 | 1.29 | 0.37 |

*Time elasped in minutes between substrate application to the membrane and washing the membrane with stop solution (50 mM EDTA). The sample and the conjugate were each applied for 1 minute.

From Table 2, it can be observed that focusing the liquid sample provides a substantial increase in the speed with which the hCG in the liquid sample binds with the immobilized anti-hCG antibody. Such improvement will allow the time necessary to perform the assays to be greatly reduced.

2. HSV Assays

HSV-2 antigen (Lee Biomolecular, Lot 86A490, $1.2 \times 10^6$ pfu/ml) was diluted in harvesting buffer (RAMP HSV Culture Confirmation Test Kit, Lot 874347, Monoclonal Antibodies, Inc.) at 1:2, 1:4, 1:8, 1:10, and 1:100. The undiluted and diluted HSV-2 antigen sample was then tested using the reaction cell described previously by either capillary focusing tube or dropwise addition. The sample volume in all cases was 25 μl. Optical density was read with the Macbeth TD904 Transmission Densitometer, as previously described, and the results are set forth in Table 3.

TABLE 3

| HSV Ag Conc. (pfu/ml × $10^5$) | ΔO.D. Capillary | ΔO.D. Dropwise |
|---|---|---|
| 0 | 0.02 | 0.01 |
| 0.12 | 0.05 | 0.02 |
| 1.20 | 0.11 | 0.02 |
| 1.50 | 0.16 | 0.03 |
| 3.00 | 0.32 | 0.02 |
| 6.00 | 0.76 | 0.02 |
| 12.00 | 0.83 | 0.04 |

As with the hCG assay, the focused sample assay of the present invention provides substantially improved sensitivity. Indeed, even at the highest HSV Ag concentration, the color signal produced by dropwise sample addition was barely visible, while that produced by capillary tube addition was easily observed.

In performing the focused sample assays as just described, it was observed that the liquid sample would wet the are immediately surrounding the area contacted by the capillary port. Surprisingly, however, the analyte in the liquid sample (hCG and HSV) did not spread with the liquid sample so that the area of color change produced by developing the membrane was limited to the area contacted by the capillary port. Such focusing of the analyte provides a sharply defined visual signal that can be easily detected.

Although the foregoing invention has been described in some detail by way of illustration and example of purposes of clarity of understanding, it will be obvious that certain changes and modifications may be practiced within the scope of the appended claims.

What is claimed is:

1. An assay method for determining the presence of an analyte in a liquid sample, said method employing:
   a reaction cell including a microporous membrane and an absorbent in liquid receiving relationship with the membrane;
   an applicator separate from the reaction cell and having a port with an open area in the range from about 0.5 mm² to 20 mm², said area being substantially less than the area of the membrane; and
   a reagent system including components capable of interacting with analyte immobilized within the microporous membrane to produce a visual signal;
   said method comprising:
   applying to the membrane of the reaction cell in a predetermined order (1) a preselected volume of sample, and (2) the components of the reagent system, wherein at least one of the sample and the components is applied using the applicator, the port of the applicator being contacted with the membrane to limit outward diffusion of the analyte within the membrane, whereby a visual signal is produced having the dimensions of the port; and observing the entire surface of the membrane to determine if the visual signal has been produced.

2. An assay method as in claim 1, wherein the applicator is a capillary tube and the sample or component is drawn from the tube by capillary action without pressurization.

3. An assay method as in claim 1, wherein the membrane and the absorbent in the reaction cell are separated by a porous, non-absorbent layer which remains substantially free from color development, whereby color which develops in the absorbent is visually blocked from the membrane.

4. An assay method as in claim 1, wherein the sample volume is in the range from about 1 μl to 1000 μl.

5. An assay method as in claim 1, wherein the reagent system produces a color signal.

6. An assay method as in claim 5, wherein the reagent system includes an enzyme and enzyme substrate.

7. An assay method as in claim 1, wherein the reagent system produces a fluorescent signal.

8. An assay method as in claim 1, wherein the applicator port has an area in the range from about 1 mm² to 10 mm².

9. An assay method as in claim 8, wherein the applicator port is generally circular having a diameter in the range from 1 mm to 3 mm.

10. An assay method as in claim 1, wherein the membrane includes an immobilized substance capable of specifically binding the analyte.

11. An assay method as in claim 10, wherein the substance is an antibody specific for the analyte.

12. An assay method as in claim 1, wherein the membrane is substantially free from specifically binding substances and blocked against non-specific binding.

13. An assay method as in claim 1, wherein c control sample is applied to a second area on the membrane prior to addition of the components of the reagent system required for production of the visual signal, whereby the signal resulting from the liquid sample may be compared to that resulting from the control sample.

14. An assay method as in claim 1, wherein the analyte is selected from the group consisting of antigens, antibodies, haptens, drugs, hormones macromolecules, toxins, bacteria, viruses, enzymes, tumor markers, and nucleic acids.

15. An assay method as in claim 1, wherein the applicator is a capillary tube.

16. An assay method as in claim 1, wherein the applicator is a focusing tube.

17. An assay method as in claim 16, wherein the focusing tube includes at least two ports, wherein each of the ports will contact a different area on the membrane.

18. An assay method as in claim 17, wherein different samples are applied through each of the ports.

19. An assay method as in claim 17, wherein different reagent system components are applied through each of the ports.

20. An assay method for determining the presence of an analyte in a liquid sample, said method comprising:
   passing a predetermined volume of the sample through a limited area in the range from about 0.5 mm² to 20 mm² on a microporous membrane capable of immobilizing the analyte, wherein the exposed area of the membrane is sufficiently greater than the limited area to allow visualization of the sample on the limited area in contrast to the remaining area of the membrane;

applying to the entire membrane surface in a predetermined order components of a reagent system capable of interacting with analyte immobilized on the microporous membrane to produce a visual signal within said well-defined area only; and observing the membrane to determine if a visual signal has been produced within the limited area.

21. An assay method as in claim 20, wherein the sample is passed through the membrane by contacting one face of the membrane with a capillary tube holding a predetermined volume of sample and absorbing the sample with an absorbent placed against the other face of the membrane.

22. An assay method as in claim 20, wherein the membrane includes an immobilized substance capable of specifically binding the analyte.

23. An assay method as in claim 22, wherein the substance is an antibody specific for the analyte.

24. An assay method as in claim 20, wherein the membrane is substantially free from specifically-binding substances.

25. An assay method as in claim 20, wherein the sample volume is in the range from about 1 $\mu$l to 1000 $\mu$l.

26. An assay method as in claim 20, wherein the reagent system produces a color signal within said limited area.

27. An assay method as in claim 26, wherein the reagent system includes an enzyme and enzyme substrate.

28. An assay method as in claim 20, wherein the reagent system produces a fluorescent signal.

29. An assay method as in claim 20, wherein the analyte is selected from the group consisting of antigens, antibodies, haptens, drugs, hormones, macromolecules, toxins, bacteria, viruses, enzymes, tumor markers, and nucleic acids.

30. An assay method as in claim 20, wherein the sample is passed through the membrane by contacting one face of the membrane with a focusing tube and applying liquid sample through the focusing tube, said sample being absorbed by an absorbent placed against the other face of the membrane.

31. An assay kit comprising:
a reaction cell including a microporous membrane and an absorbent in liquid receiving relationship with the membrane;
an applicator separate from the reaction cell and having a port with an open area in the from range from about 0.5 mm$^2$ to 20 mm$^2$, said area being substantially less than the area of the membrane;
a reagent system including components capable of interacting with analyte immobilized within the microporous membrane to produce a visual signal; and instructions to apply to the membrane of the reaction cell in a predetermined order (1) a preselected volume of sample, and (2) the components of the reagent system, wherein at least one of the sample and the components is applied using the applicator with the port in contact with the membrane to limit outward diffusion of the sample within the membrane; and to observe the membrane to determine if a visual signal has been produced.

32. An assay kit as in claim 31, wherein the applicator is a capillary tube.

33. An assay kit as in claim 31, wherein the membrane and the absorbent in the reaction cell are separated by a porous, non-absorbent layer which remains substantially free from color development, whereby color which develops in the absorbent is visually blocked from the membrane.

34. An assay kit as in claim 31, wherein the reagent system produces a color signal.

35. An assay kit as in claim 34, wherein the reagent system includes an enzyme and enzyme substrate.

36. An assay kit as in claim 31, wherein the reagent system produces a fluorescent signal.

37. An assay kit as in claim 31, wherein the membrane includes an immobilized substance capable of specifically binding the analyte.

38. An assay kit as in claim 37, wherein the substance is an antibody specific for the analyte.

39. An assay kit as in claim 31, wherein the membrane is substantially free from specifically-binding substances.

40. An assay kit as in claim 31, wherein the analyte is selected from the group consisting of antigens, antibodies, haptens, drugs, hormones, macromolecules, toxins, bacteria, viruses, enzymes, tumor markers, and nucleic acids.

41. An assay kit as in claim 31, wherein the applicator is a focusing tube.

42. An assay kit as in claim 41, wherein the applicator tube includes at least two ports, wherein each of the ports will contact a different area on the membrane.

43. An assay kit as in claim 42, wherein the instructions state to apply different samples through each of the ports.

44. An assay kit as in claim 42, wherein the instructions state to apply different reagent system components through each of the ports.

45. An assay method as in claim 1, wherein the exposed membrane area is in the range from about 0.2 cm$^2$ to 2 cm$^2$.

46. An assay method as in claim 20, wherein the exposed membrane area is in the range from about 0.2 cm$^2$ to 2 cm$^2$.

47. An assay kit as in claim 31, wherein the membrane has an exposed area in the range from about 0.2 cm$^2$ to 2 cm$^2$.

* * * * *